United States Patent [19]

Munson et al.

[11] 4,072,148
[45] Feb. 7, 1978

[54] MULTISTAGE MIXING VALVE FOR A MEDICAL RESPIRATOR

[75] Inventors: Ramon Jon Munson, Rialto; Claude Calvert Hurd; James Weigl, both of Riverside, all of Calif.

[73] Assignee: Bourns, Inc., Riverside, Calif.

[21] Appl. No.: 756,448

[22] Filed: Jan. 3, 1977

[51] Int. Cl.² ............................................. A61M 16/00
[52] U.S. Cl. ................................ 128/142.2; 128/209; 128/210; 137/601; 137/607
[58] Field of Search ............... 128/145.8, 145.7, 145.6, 128/145.5, 142 R, 142.2, 142.3, 147, 203, 191 R, 188, 209, 210, 211, 196, 197; 137/601, 607, 599

[56] References Cited

U.S. PATENT DOCUMENTS

| | | | |
|---|---|---|---|
| 3,586,053 | 6/1971 | Browning | 137/607 X |
| 3,669,134 | 6/1972 | Dobritz | 128/145.8 X |
| 3,693,653 | 9/1972 | Cramer et al. | 137/557 |
| 3,807,425 | 4/1974 | Boirum et al. | 137/110 |
| 3,809,109 | 5/1974 | Breiling et al. | 137/607 X |
| 3,817,085 | 6/1974 | Stubbs | 128/142 X |
| 3,896,837 | 7/1975 | Rahling | 137/110 |

Primary Examiner—Robert W. Michell
Assistant Examiner—Henry J. Recla
Attorney, Agent, or Firm—Paul H. Ware; William G. Becker

[57] ABSTRACT

A valve assembly for mixing air and oxygen in a medical respirator over a wide range of volumetric flow rates, without sacrificing relative mixing accuracy at the lower flow rates. The assembly is divided into a plurality of mixing valve modules characterized respectively by progressively increasing volumetric flow capacities and progressively decreasing absolute mixing accuracies. The higher flow capacity modules are sequentially brought into operation as the overall valve flow increases and then interrupted when the flow decreases below a threshold level associated with each module. The valve assembly accordingly has a large range of flow capacities without degrading absolute mixing accuracy during low flow rate conditions by the effect of the higher capacity modules.

9 Claims, 4 Drawing Figures

MULTISTAGE MIXING VALVE FOR A MEDICAL RESPIRATOR

BACKGROUND OF THE INVENTION

1. Field of the Invention

This invention relates to gas mixing valves, and more particularly to mixing valves adapted for use in a medical respirator.

2. Description of the Prior Art

The task of mixing air and oxygen in desired ratios for medical respirators is complicated by the fact that the air and oxygen supplies are usually subject to pressure fluctuations, and do not remain consistently in balance. This is not a significant problem at high flow rates when the pressure drop across the mixing valve is considerably larger than the expected range of imbalance between the two gas sources. However, as the volumetric gas flow rate decreases and the pressure drop across the valve correspondingly decreases, the effect of air and oxygen supply pressure imbalance on the mixing accuracy is greatly increased. While a high capacity mixing valve may have a relative mixing accuracy comparable to the relative mixing accuracy of smaller capacity valves, i.e., each valve is characterized by comparable percentage errors in the mixing accuracies, the larger capacity valves are inherently less accurate on an absolute scale. In other words, the mixing error in liters per minute as opposed to a percentage of the total flow is worse for higher capacity than for lower capacity valves. This becomes a problem should an attempt be made to operate a larger valve at a lower flow rate, since the absolute error caused by fluctuations in the gas supply pressures will then become significant in proportion to the total flow. Although mixing accuracy can be enhanced by the use of a relatively small scale valve, this unduly limits the range of flow rates over which the valve is capable of operating.

An approach toward solving this problem is described in U.S. patent application Ser. No. 677,344, assigned to the assignee of the present invention. In this application the dimensions of the orifices through which air and oxygen flow into the valve are variable in a first direction to adjust the mixing ratio. The orifice dimensions are also variable in a second direction in response to a pressure sensitive device to adjust the overall area through which the gases flow into the valve. The reduction in accuracy during low flow rates is thereby substantially overcome by decreasing the size of both inlet orifices, which in turn increases the pressure drop across the orifices. This pressure sensing function is performed by a diaphragm which adjusts the dimensions of the air and oxygen orifices by equal proportionate amounts.

While the above type of mixing valve represents a significant improvement, its components require careful machining in order to achieve the necessary close tolerances. There is still a need, however, for a lower cost gas mixing valve which combines an ability to operate over a wide range of flow rates with an improved absolute mixing accuracy at the lower flow rates.

SUMMARY OF THE INVENTION

In view of the above stated problems associated with the prior art, the principal object of the present invention is the provision of a novel, lower cost gas mixing valve which may be used in a medical respirator to mix air and oxygen over a wide range of flow rates with improved performance at the lower end of the range.

An additional object is the provision of such a mixing valve capable of operating in separate high and low gas flow modes, with the low flow mode eliminating those high flow rate components which cause the low absolute mixing accuracy.

These and other objects are accomplished according to the present invention by a mixing valve assembly comprising a plurality of mixing valve modules characterized respectively by progressively increasing volumetric flow capacities and progressively decreasing absolute mixing accuracies. Each module includes a plurality of inlet ports adapted to receive gas from the sources, an outlet port, and a gas mixing means between the inlet and outlet ports which controls the mixing ratio. The mixing ratios of the various modules are adjustable by substantially equal amounts, permitting a single outflow having the desired mixture to be produced by coupling all the outlet ports together. Each of the modules other than the one having the lowest flow capacity is provided with a gas flow inhibiting means which prevents gas from flowing through the modules until the total gas flow through the valve exceeds a predetermined threshold level. The threshold level for each module is set proportional to the flow capacity of the module, whereby the valve flow capacity decreases in steps as the gas flow rate decreases. This in turn compensates for the otherwise decreasing pressure differential across the valve to enhance mixing accuracy at the lower flow rates.

In a preferred embodiment designed for use with a medical respirator, the mixing valve has two modules or stages of ball valve type construction. The valve balls are mutually coupled for common movement, permitting both stages to be adjusted by means of a single adjustment member. Flow is interrupted in the larger capacity valve for flows below the threshold level by means of a diaphragm which responds to the outlet port pressure to open or shut a cutoff valve.

DESCRIPTION OF THE DRAWINGS

These and other objects and features of the invention will become apparent to those skilled in the art from the ensuing detailed description thereof, taken together with the accompanying drawings, in which.

DESCRIPTION OF A PREFERRED EMBODIMENT

Figure 1:
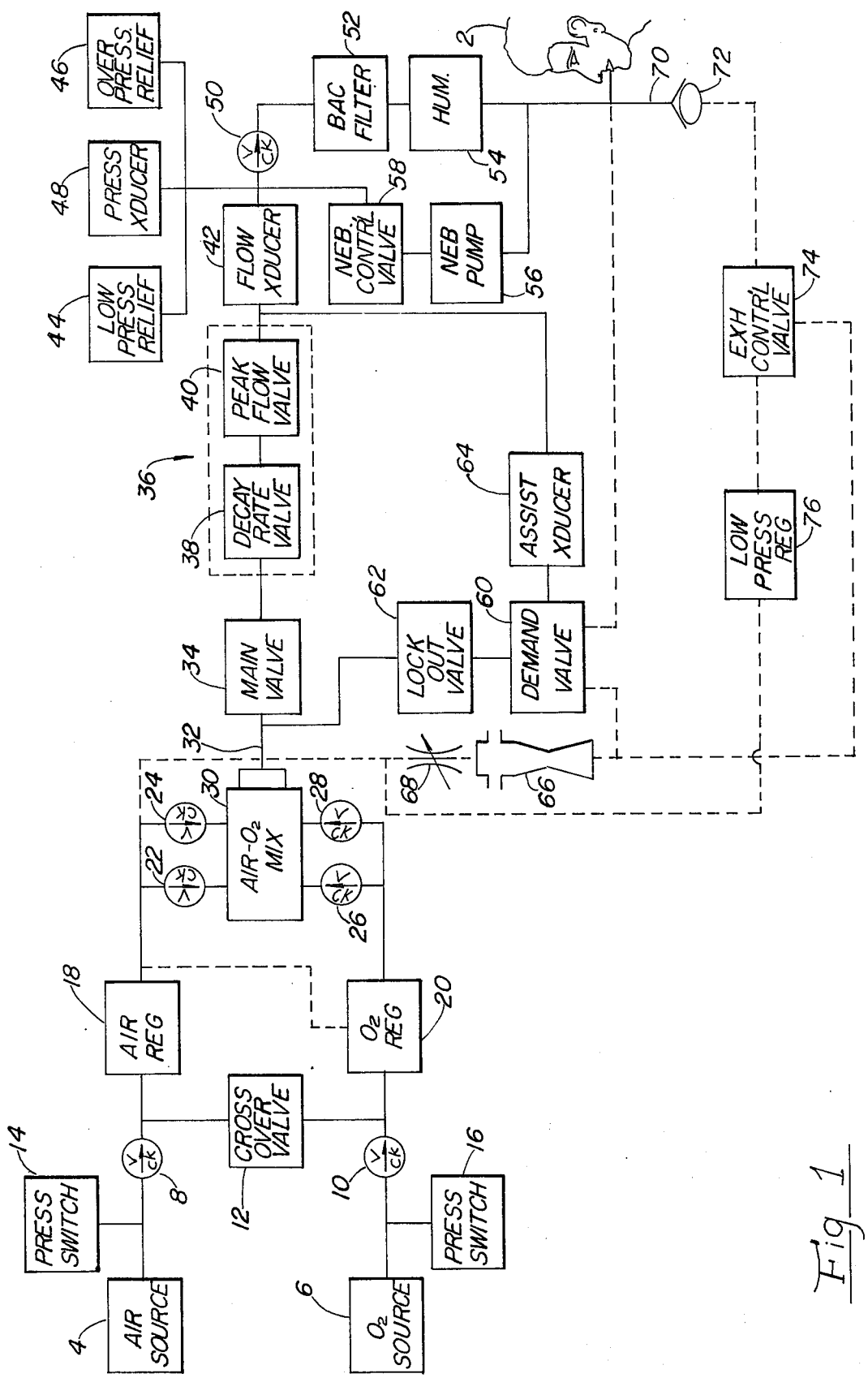
FIG. 1 is a pneumatic flow diagram of a medical respirator in which the improved mixing valve is employed.

FIG. 1 illustrates the pneumatic operation of a medical respirator which employs the improved mixing valve of the present invention. Principal conduits which support the flow of breathing air to a patient 2 are indicated by solid lines, while pilot lines serving principally to establish pressures at various locations within the respirator are indicated in dashed lines. Starting from the left-hand side of the figure, ambient air and oxygen are delivered from appropriate sources 4 and 6 through check valves 8 and 10 to opposite sides of a cross-over valve 12, which valve is opened by pressure switches 14 and 16 in case one of the sources is lost to ensure that the patient receives at least some breathing air. A regulator 18 in the airline establishes a desired line pressure, typically about 10 psi, with a relay 20 in the oxygen line slaved to regulator 18 to keep the oxygen line at the same pressure. The air and oxygen are delivered through check valves 22, 24, 26 and 28 to the mixing valve or blender 30 which comprises the subject of this invention. Valve 30 combines the input gases in desired proportions and supplies an outflow of breathing gas through conduit 32. Briefly stating its principal of operation, valve 30 employs a first stage which operates continuously and a second stage which operates only for large air flows, with the two stages combining to give accurate blending over a wide range of flow rates.

Continuing with the main air flow, conduit 32 branches with one branch going to a main valve 34. With a respirator having facilities for multiple modes of operation, valve 34 can be used in both a control mode, in which a predetermined volume of breathing gas is delivered to the patient at set intervals, and in an assist mode, in which the valve is opened by a patient's attempt to breathe rather than at fixed intervals. The main valve output is processed through valve assembly 36, comprising a decay rate regulator or valve 38 which controls the rate at which periodic flows of breathing gas decay from a peak value, and a peak flow valve 40 which controls the maximum rate of flow to the patient. A flow transducer 42 downstream from valve assembly 36 measures the gas volume delivered to the patient and closes main valve 34 when the desired volume has been delivered. Connected to the output of flow transducer 42 are low and high pressure relief valves 44 and 46, and a pressure transducer 48 which activates appropriate alarms for adverse pressure conditions. The output of flow transducer 42 is delivered to the patient through a check valve 50, bacteria filter 52, and humidifier 54. Various medications may be added to the breathing gas flow by a nebulizer pump 56, which is deactivated during patient exhalation by a control valve 58.

An alternate flow path from mixing valve 30 is provided for a demand mode, i.e., a mode in which the respirator permits the patient to breathe on his own without delivering positive air flows. This path begins at the other branch of conduit 32 and includes a demand valve 60 which maintains the pressure in the system above a certain minimum amount to prevent the patient's lungs from becoming unduly depressurized, a valve 62 which locks out demand valve 60 in the control mode, and an assist transducer 64 which operates in the assist mode to detect breath attempts and actuate main valve 34 in response thereto. Assist transducer 64 is connected to the output of valve assembly 36 so that breathing air flows in all modes are treated for bacteria, humidity, and medications. Other aspects of the respirator include a venturi 66 with a variable orifice 68 for maintaining a positive pressure on demand valve 60 and thereby establishing a positive expiratory end pressure, an exhaust 70 for expired air, and an expandable bladder 72 which blocks exhaust 70 during patient inhalation and collapses during exhalation. Bladder 72 is operated by a three-way exhalation control valve 74 which connects the bladder to the regulated pressure of venturi 66 during expiration, and to a low pressure regulator 76, supplied by regulator 18, during inspiration.

Having described the general features of a respirator in which the subject mixing valve may be incorporated, it should be noted that the valve is not limited to such an application, but rather may be employed with other systems in which it is necessary to accurately mix a plurality of gases.

Figure 2:
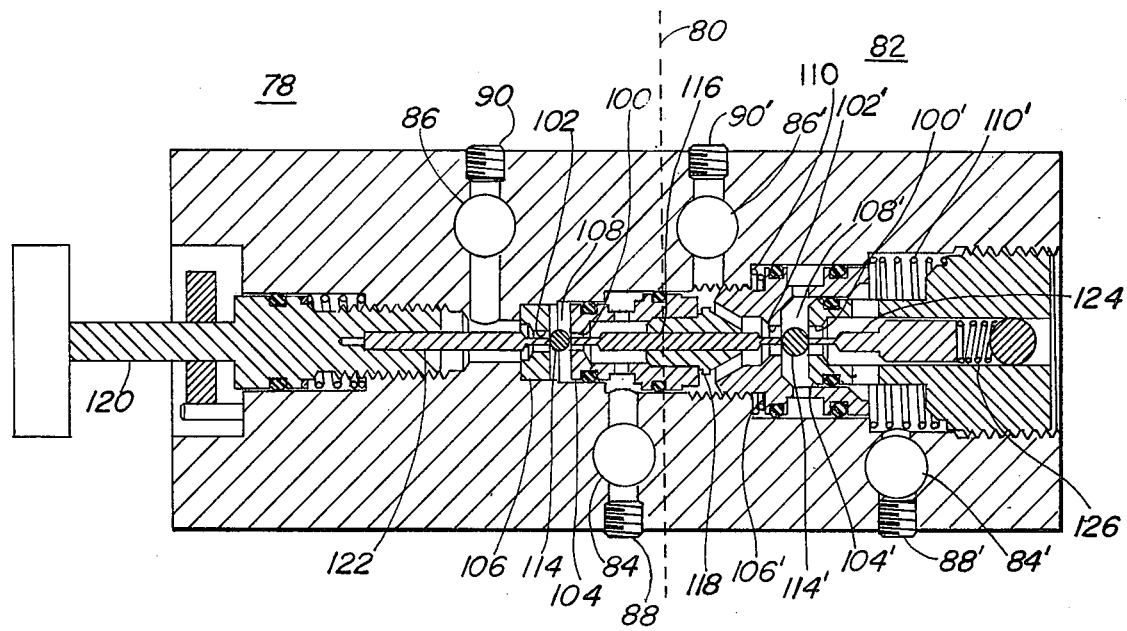
FIG. 2 is a sectional view of the mixing valve indicated in FIG. 1.
Figure 3:
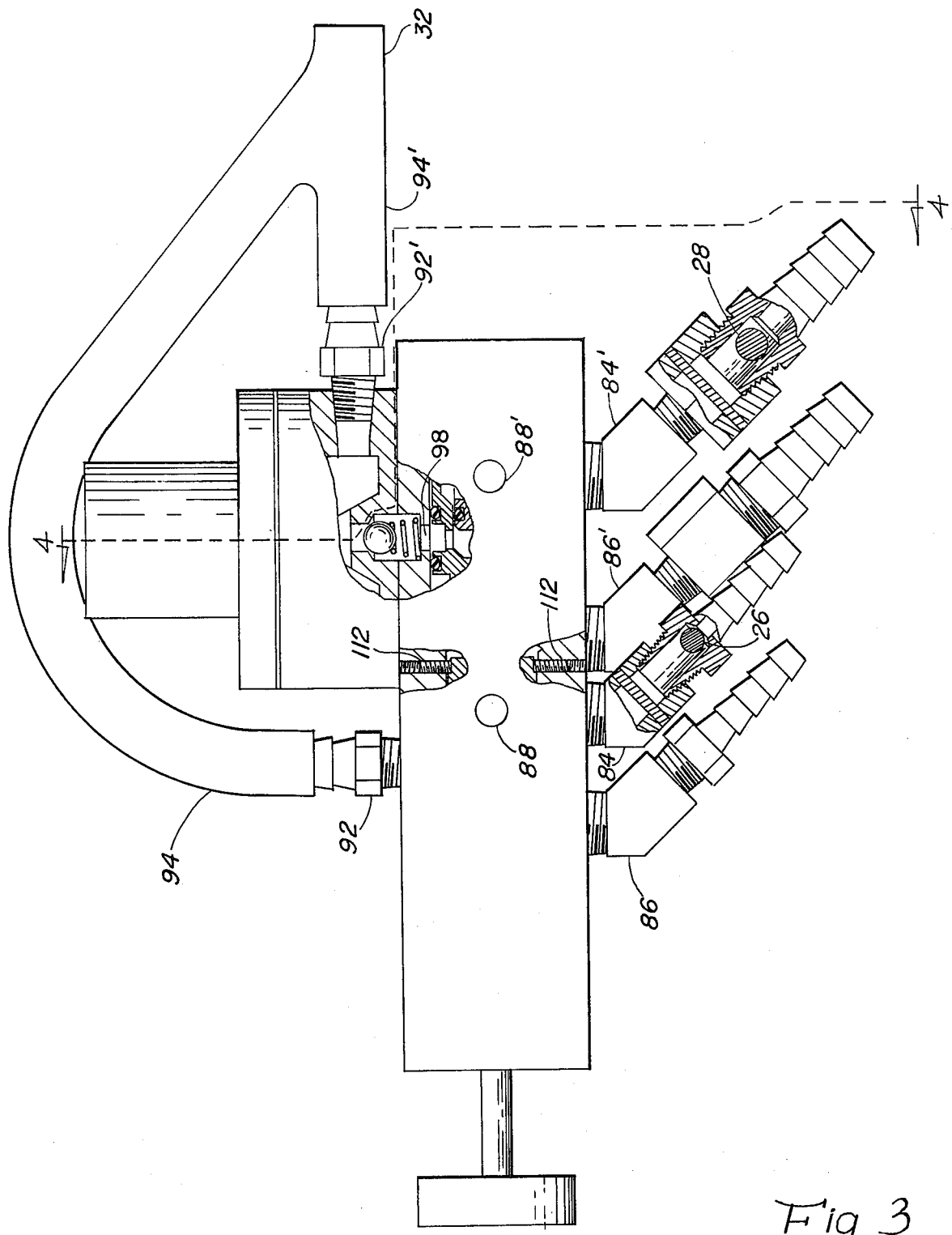
FIG. 3 is a partially sectioned elevation view of the valve.

Referring to FIGS. 2 and 3, the illustrative mixing valve shown comprises two valve stages, one of which is operated continuously and the other of which operates only at higher flow rates. Additional stages could be added to further increase the range of the valve, but for use with a medical respirator two stages are generally sufficient. The first stage 78 is located to the left of dividing line 80 in FIG. 2, with the second stage 82 located to the right of the line. Since the two stages are of similar construction, the same reference numerals will be used for corresponding components of each, with a prime symbol used to indicate components in the second valve. Oxygen and air inlet ports 84, 84' and 86, 86', respectively, receive gas from the gas sources and transmit it to the interior of the valve. Oxygen inlet check valves 26 and 28, which are necessary to prevent back flows of oxygen in case the oxygen pressure fluctuates below the air pressure, are indicated in FIG. 3. Air inlet check valves 22 and 24 are provided at corresponding locations in the air inlets. The inlet ports extend out from the bottom of the valve housing, and are accessible through openings in the sides of the housing which are normally closed by plugs 88, 88', 90, and 90'. The gases leave the two mixing valve stages in a mixed state through outlet ports 92, 92'. The flows through these ports are carried by plastic tubing 94, 94', combined downstream from the valve in conduit 32, and conducted through the conduit to main valve 34 discussed above.

The two valves are of similar ball-valve construction, the principal difference being that the second valve 82 is larger and has a greater gas flow rate capacity. On the other hand, while the relative mixing accuracy of the second valve in percent may be close to that of the first valve, its larger dimensions cause it to have a generally lower absolute mixing accuracy.

The oxygen and air inlets respectively communicate through the valve structure with orifices 100, 100' and 102, 102', which are disposed in mutual opposition through metal members 104, 104' and 106, 106'. Interior chambers 108, 108' are formed between the members. In order to ensure precise spacings between members 104, 104' and 106, 106', members 106, 104 are first cemented into place, and members 104', 106' then threaded into appropriate bores in the valve housing and held against any movement relative to the threads by springs 110, 110'. When they are correctly positioned, member 104' is cemented in place and member 104 is locked in place with screws 112.

Valve balls 114, 114' are held between orifices 100, 100' and 102, 102' on opposite ends of a rod 116 which longitudinally slides within a packing 118. The position of balls 114, 114', with respect to their opposed orifices determines the ratio of air and oxygen supplied to the patient; moving the balls all the way to the left against air orifices 102, 102' blocks those orifices and produces a 100% oxygen flow, while 100% air flow is attained by moving the balls all the way to the right to block the oxygen orifices 100, 100'. A desired mixture of gases is achieved by appropriately positioning the balls between orifices 100, 100' and 102, 102'. Since it is desirable that the two balls be controlled by a single adjustment mechanism, the two valve stages are dimensioned such that both balls traverse equal distances in going from a position completely blocking one orifice to a position completely blocking the other orifice.

The position of the valve balls is controlled by an adjustment stem 120 threaded into the valve housing and carrying a pin 122 at its inner end which bears against ball 114. Clockwise rotation of stem 120 moves pin 122 to the right, which in turn moves balls 114, 114' to the right to increase the air/oxygen ratio by increasing the gas flow through orifices 102, 102' and decreasing it through orifices 100, 100'. At the opposite end of the housing another pin 124 bears against ball 114' and urges it to the left, under the influence of a spring 126, to return the valve balls to the left when the adjustment stem is rotated counterclockwise. Both valve stages are accordingly subject to common control by a single adjustment member so that their mixing ratios are maintained substantially equal.

Figure 4:
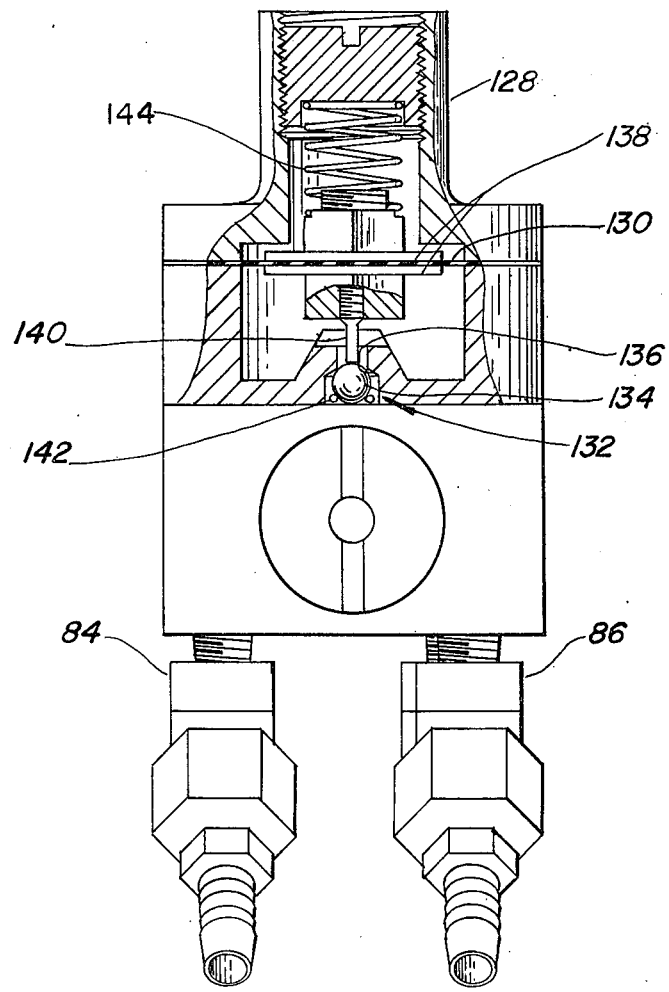
FIG. 4 is a partially sectioned view taken along the lines 4—4 of FIG. 3.

Referring now to FIG. 4, a mechanism is shown by which the second stage is made operational for higher flow rates but is interrupted during low flow rates, leaving the first stage to handle the entire flow. A superstructure 128 extends up from the second stage with an interior compartment. A flexible resilient diaphragm 130 held around its periphery by the superstructure divides the compartment into upper and lower portions and is free to flex vertically. Mixed gas flowing from the second stage valve passes through the compartment section below diaphragm 130 before reaching outlet port 98. A cutoff valve 132, comprising a ball 134 seatable against an orifice 136 in the gas flow path, controls the flow of gas to outlet 92'. A pair of metal plates 138 are affixed to the upper and lower surfaces of the diaphragm at its center, with a pin 140 screwed through the plate and extending to the top of ball 134. The ball is urged by a spring 142 toward a seated position closing orifice 136.

In operation, the chamber above diaphragm 130 is maintained at a reference pressure, which may be atmospheric, such that a drop in pressure beneath the diaphragm causes the diaphragm to flex downwardly and unseat ball 134, thereby permitting mixed gas to flow through the second stage mixing valve. This situation occurs when relatively large flows of gas are being delivered to the patient, and results in gas being processed through both valve stages. As the patient approaches the end of an inhalation the inhalation rate drops, causing the pressure in both conduit 32 and second stage outlet port 98 to increase. The pressure below diaphragm 130 accordingly increases, lifting pin 140 and permitting ball 134 to close the valve orifice under the urging of spring 142. This terminates the flow of gas through outlet port 98 and effectively cuts off the second mixing valve stage, directing the entire gas flow to the patient through the first stage. In this mode the danger of poor mixing accuracy due to fluctuations in the gas source pressures is greatly reduced, since the increased flow through the first mixing valve stage produces a corresponding increase in the pressure differential across the valve. Supply pressure fluctuations accordingly are less significant because of the greater mixing valve pressure differential.

With the described mixing valve, accurate air/oxygen mixtures can be obtained at any flow rate between 15 and 120 liters per minute. It has been found advantageous to have cutoff valve 132 operate at a threshold flow rate between 40 and 60 liters per minute, so that both stages are operating at flow rates above the threshold with only with first stage operating at flow rates below the threshold. The threshold level can itself be made variable simply by adjusting the spring 144 such that it increases or decreases the force on diaphragm 130.

It should be apparent that, while the two-stage mixing valve described above is well suited for installation in medical respirators, numerous variations and modifications are possible. For example, the principals of the invention can be applied in mixing a greater number of gases over a greater range of flow rates by selecting appropriately designed valves for the number of gases to be handled, and adding as many additional valve modules of progressively increasing flow capacity and decreasing absolute accuracy as are necessary. It is therefore intended that the scope of the invention be limited only in and by the terms of the appended claims.

What is claimed is:

1. A valve for accurately mixing gases from a plurality of separate gas source means over a range of volumetric flow rates, said gas source means each being characterized by nominally equal but fluctuating pressure levels, comprising:

a plurality of serially arranged mixing valve modules, each respective module including means providing a greater volumetric flow capacities and a lesser absolute mixing accuracy than the preceding valve module, each of said modules including a plurality of inlet ports each adapted to receive a gas from one of said gas sources, an outlet port, and gas mixing means between each said inlet ports and said outlet port for controlling the ratio of said separate gases flowing through the module, each outlet port of each module being mutually coupled to provide a single valve outlet, means for adjusting the mixing ratio of each of said modules by substantially equal amounts, and for each of said modules other than the module having the lowest flow capacity and highest absolute mixing accuracy, means for permitting gas flow through said module until the total volumetric gas flow through said valve exceeds a predetermined threshold, the threshold level for each module varying in positive proportion to the volumetric flow capacity of said module.

2. The valve of claim 1, said valve being adapted to mix gases from first and second gas sources, wherein each of said valve modules comprises a ball valve means including first and second opposed orifices communicating respectively with the inlet ports for said first and second gas sources, a ball moveable between positions at least partially blocking each of said orifices so as to establish a mixing ratio for said module, and adjustment means for moving said ball.

3. The valve of claim 2, wherein the valve balls are mutually coupled for common movement, and the adjustment means for said valves comprises an adjustment member adapted to move against and adjust the positions of said coupled valve balls.

4. In a medical respirator having nominally constant-pressure air and oxygen sources, conduit means for delivering gas from said sources to a patient, and control means controlling the supply of gas from said sources to said conduit means, wherein the improvement comprises a two-stage mixing valve for accurately setting the air/oxygen mixture of breathing gas delivered to the patient over a range of volumetric flow rates, despite fluctuations in the actual pressures of said sources, said two-stage valve comprising:

first and second mixing valves, each of said mixing valves including air and oxygen inlet ports adapted to receive gas from said sources, an outlet port adapted to be connected to said conduit means, and means for controlling the air/oxygen mixing ratio, said first mixing valve having a greater absolute mixing accuracy but lower volumetric flow capacity than said second mixing valve, means for adjusting the mixing ratios of each of said mixing valves, and means between said second mixing valve outlet port and said conduit adapted to sense the pressure in said conduit means and interrupt gas flow through said second mixing valve when the sensed pressure exceeds a predetermined threshold level indicative of a low gas flow condition, whereby said first mixing valve acts alone during low flow rate conditions to achieve a high absolute mixing accuracy when the pressure differential across said mixing valves is relatively small, and said first and second mixing valves act together during high flow rate conditions to achieve a lower absolute but comparable relative mixing accuracy when said pressure differential is relatively high.

5. The invention of claim 4, said flow interruption means comprising the combination of a cutoff valve means governing the flow of gas through the outlet port of the second mixing valve, and pressure sensitive means controlling said cutoff valve.

6. The invention of claim 5, said cutoff valve means comprising a flow orifice and means for blocking said orifice, and said pressure sensitive control means comprising the combination of a flexible, resilient diaphragm having one side exposed to the pressure in the outlet port for the second mixing valve, a reference pressure chamber on the other side of said diaphragm, means coupled to said diaphragm and moveable thereby against said blocking means to move said blocking means away from said orifice when said outlet port pressure is less than said threshold pressure, and spring means urging said blocking means to a position blocking said orifice when said outlet port pressure exceeds said threshold level.

7. The invention of claim 6, said diaphragm-coupled means comprising a pin extending from said diaphragm toward said blocking means, and further including means for adjusting the reach of said pin relative to said diaphragm and thereby the operating threshold level of said second mixing valve.

8. The invention of claim 4, wherein said first and second mixing valves each comprise ball valve constructions which include a ball disposed between a pair of orifices, said orifices communicating respectively with said air and oxygen inlet ports to receive gas therefrom, said means for adjusting the mixing ratios adjusts the positions of said valve balls between said orifices establishing the air/oxygen mixture for said mixing valves.

9. The invention of claim 8, wherein said valve balls are mutually coupled for common movement to substantially equalize the mixing ratios of said first and second valves, and said valve adjustment means comprises a control member adapted to move against and adjust the positions of said coupled valve balls.

* * * * *